US005478307A

United States Patent [19]

Wang

[11] Patent Number: 5,478,307

[45] Date of Patent: Dec. 26, 1995

[54] APPARATUS FOR FOOT TRACTION

[76] Inventor: Chun-Jong Wang, 9, Lane 1096, Chun Jih Road, Taoyuan, Taiwan, Taiwan

[21] Appl. No.: 266,371

[22] Filed: Jun. 27, 1994

[51] Int. Cl.[6] .......... A61F 5/00

[52] U.S. Cl. .......... 602/32; 606/245; 5/648

[58] Field of Search .......... 602/32, 33, 34, 602/35; 482/92, 142; 5/625, 626, 658, 174, 617, 624, 648, 650; 606/237, 245

[56] References Cited

U.S. PATENT DOCUMENTS

| | | | |
|---|---|---|---|
| 1,021,688 | 3/1912 | Jeune | 602/33 |
| 1,213,373 | 1/1917 | Hollowell | 602/33 |
| 1,296,128 | 3/1919 | Siebrandt | 602/33 |
| 1,837,037 | 12/1931 | Gillberg | 602/33 |
| 1,890,372 | 12/1932 | Ettinger | 602/35 |
| 2,230,620 | 2/1941 | Leiter | 602/33 |
| 2,374,163 | 4/1945 | Burchsted | 602/32 X |
| 3,117,572 | 1/1964 | Wright | 602/32 |
| 3,153,411 | 10/1964 | Unks | 602/33 |
| 3,403,675 | 10/1968 | Carr | 602/32 |
| 3,699,953 | 10/1972 | Mason | 602/34 |
| 5,025,802 | 6/1991 | Laico et al. . | |
| 5,290,219 | 3/1994 | Hetrick | 602/32 |
| 5,290,220 | 3/1994 | Guhl | 602/32 X |

*Primary Examiner*—Richard J. Apley
*Assistant Examiner*—Kim M. Lee
*Attorney, Agent, or Firm*—Bacon & Thomas

[57] ABSTRACT

An apparatus for foot traction, including a folding bed, a transmission mechanism mounted on the folding bed at the bottom, and two ankle cradles driven by the transmission mechanism to pull the user's legs, wherein the transmission mechanism consists of a transmission shaft transversely mounted on the folding bed at the bottom, a transmission cable having one end fixedly fastened to the transmission shaft in the middle and an opposite end terminating in symmetrical pairs of branch cables respectively fastened to the ankle cradles by hooks, and a handle coupled to the transmission shaft at one end is driven to turn the transmission shaft in taking up the transmission cable.

4 Claims, 3 Drawing Sheets

APPARATUS FOR FOOT TRACTION

BACKGROUND OF THE INVENTION

The present invention relates to an apparatus for foot traction which uses a transmission shaft driven by a hand wheel to take up a transmission cable so as to pull the legs by two ankle cradles.

It has been known that the effect of gravity causes the muscles of the body to be compressed vertically, and therefore the height of the body is shortened. One's height will become taller at night than in the morning. In order to release the compression caused by gravity, proper exercises are required. Various traction devices have been disclosed for pulling the legs in order to prolong body height. However, these traction devices are commonly expensive and difficult to operate.

SUMMARY OF THE INVENTION

The present invention has been accomplished in view of the above circumstances. It is therefore an object of the present invention to provide an apparatus for foot traction which helps one to effectively increase body height within a short period. It is another object of the present invention to provide an apparatus for foot traction which helps the user to release the compression force of gravity. It is still another object of the present invention to provide an apparatus for foot traction which can be conveniently operated by the user.

According to one aspect of the present invention, the apparatus comprises a folding bed, a transmission mechanism mounted on the bottom of the folding bed, and two ankle cradles driven by said transmission mechanism to pull the user's legs. The transmission mechanism consists of a transmission shaft transversely mounted on the bottom of the folding bed, a transmission cable having one end fixedly fastened to the transmission shaft in the middle and an opposite end terminating in symmetrical pairs of branch cables respectively fastened to the ankle cradles by hooks, and a handle coupled to the transmission shaft at one end and driven to turn the transmission shaft in taking up the transmission cable. According to another aspect of the present invention, a ratchet wheel is fixedly mounted around the transmission shaft, and a pawl is pivotally mounted on the folding bed and controlled to engage with the ratchet wheel so as to further stop the transmission shaft from reverse rotation.

DETAILED DESCRIPTION OF THE PREFERRED EMBODIMENT

Figure 1:
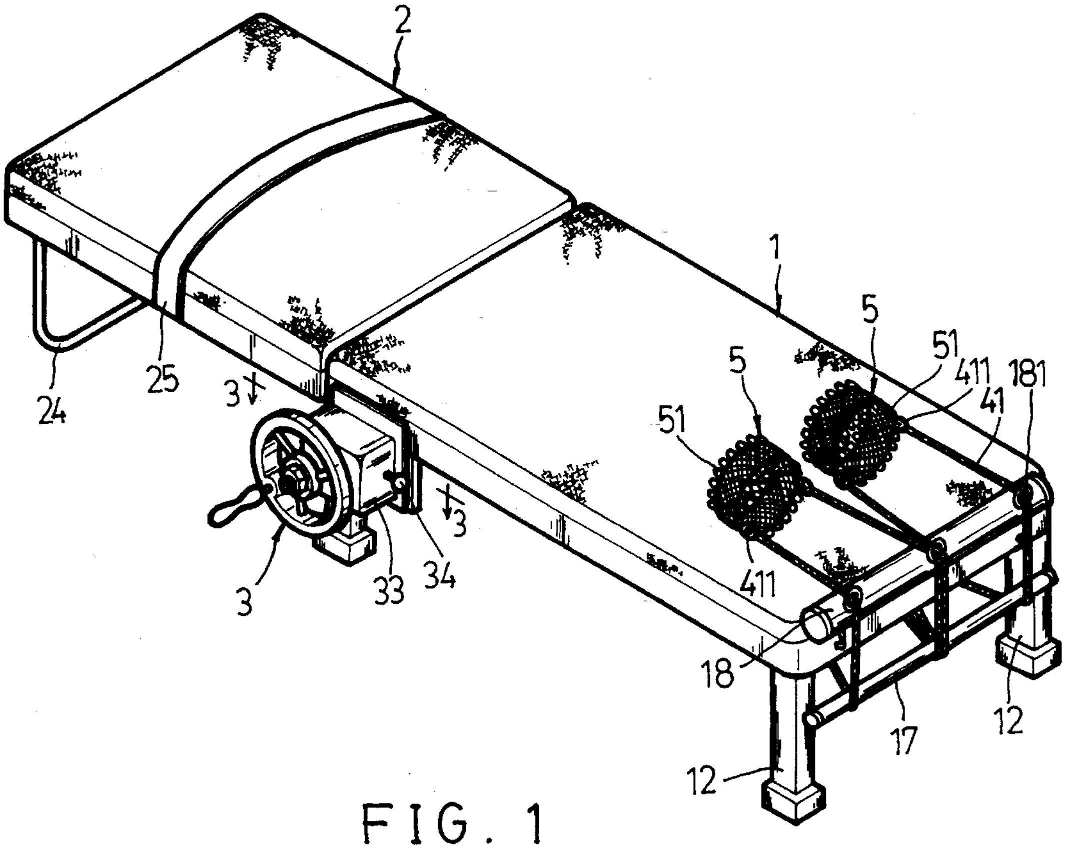
FIG. 1 is a perspective view of an apparatus for foot traction according to the present invention.
Figure 2:
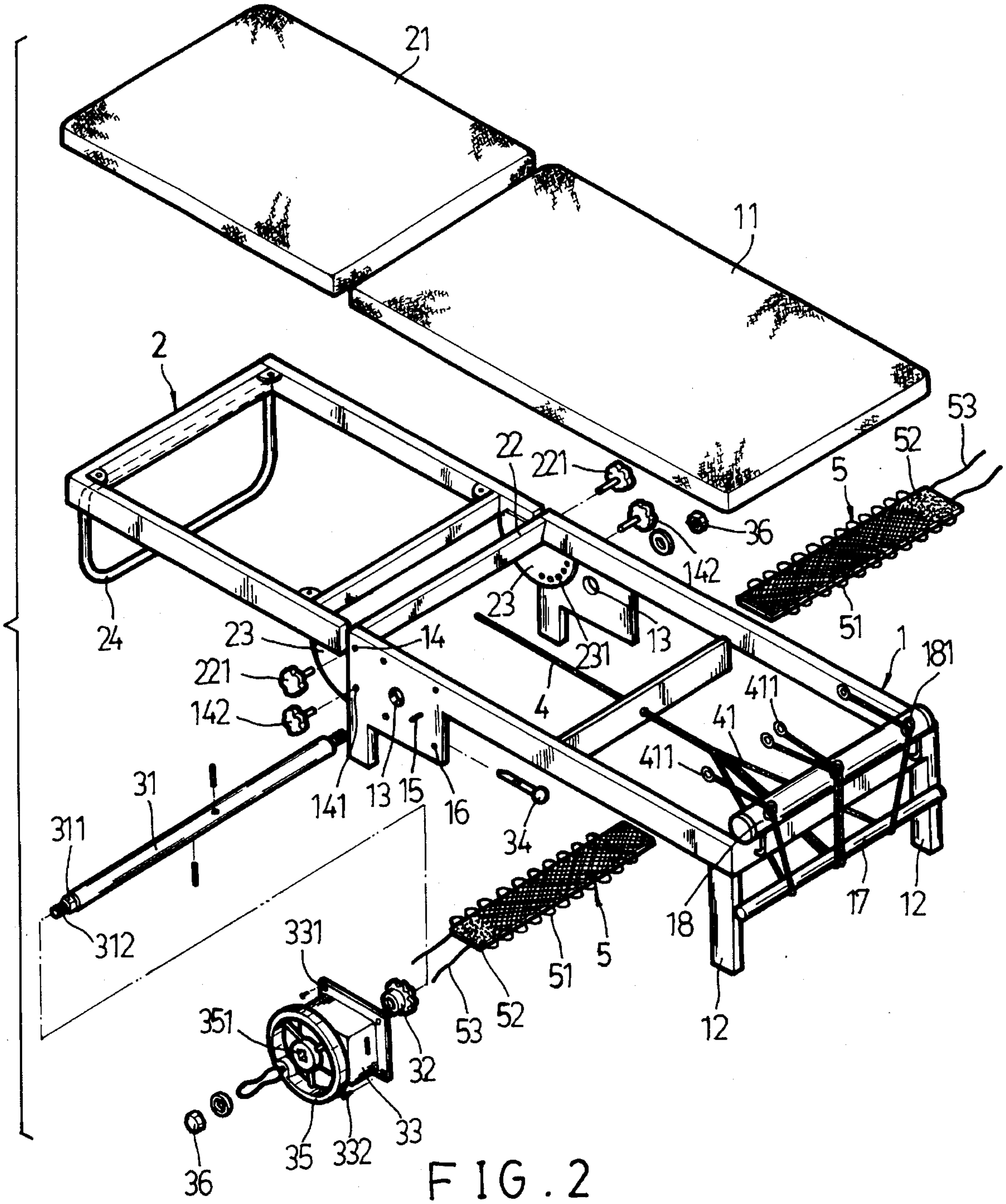
FIG. 2 is an exploded view of the apparatus shown in FIG. 1.

Referring to FIGS. 1 and 2, an apparatus for foot traction according to the present invention is generally comprised of a base frame 1, an adjustable frame 2, a transmission mechanism 3, a transmission cable 4, and two ankle cradles 5. The adjustable frame 2 is hinged to the base frame 1 at one end and can be adjusted to the desired inclination position.

The transmission mechanism 3 is fastened to the base frame 1 at one side. The transmission cable 4 is driven by the transmission mechanism 3 to pull the ankle cradles 5.

Referring to FIG. 2 again, the base frame 1 is equipped with legs 12 at the bottom and covered with a mattress 11 at the top to serve as a bed. Pivot holes 14, adjustment holes 141, and axle holes 13 are symmetrically disposed at two opposite sides. A stub rod 15 extends from one side thereof near the corresponding axle hole 13, a plurality of locating holes 16 are formed around the stub rod 15, and a link 17 and a steering rod 18 are transversely disposed at a front end opposite to the adjustable frame 2. The steering rod 18 has a plurality of through holes 181 spaced along its length. The adjustable frame 2 is covered with a mattress 21, having a strap 25 transversely disposed at the top. One end of the adjustable frame 2 is fixed with a stand 24 for supporting on the ground. The other end of the adjustable frame 2 has axle housings 22 symmetrically disposed at two opposite sides and respectively pivotally connected to the pivot holes 14 on the base frame 1 by pivot bolts 221, and two adjustment plates 23 symmetrically disposed at two opposite sides. The adjustment plates 23 have a plurality of bolt holes 231 respectively equally spaced around the axle housings 22 for selective fastening to the adjustment holes 141 by screw bolts 142, and therefore the angular position of the adjustment frame 2 can be adjusted relative to the base frame 1.

Figure 3:
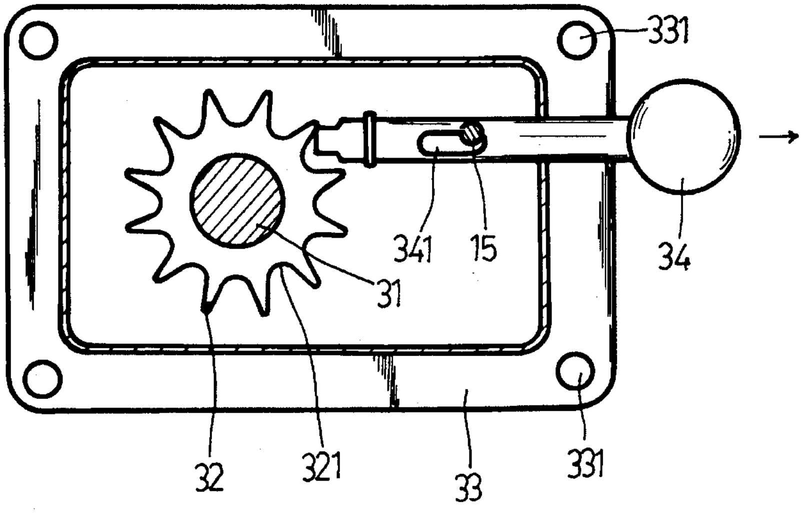
FIG. 3 is a sectional view taken on line 3—3 of FIG. 1.

The transmission mechanism 3 comprises a transmission shaft 31, a ratchet wheel 32, a ratchet wheel housing 33, a pawl 34, and a driving handle 35. The transmission shaft 31 is connected between the axle holes 13, having one end extended out of the base frame 1 and coupled to the ratchet wheel 32 within the ratchet wheel housing 33. By threading screws 332 through holes 331 on the ratchet wheel housing 33 into the locating holes 16, the ratchet wheel housing 33 is fixed to one side of the base frame 1. The pawl 34 has an elongated slot 341 in the middle mounted on the stub rod 15, and is moved to engage a pitch 321 between any two adjacent teeth of the ratchet wheel 32 to stop the ratchet wheel 32 from reverse rotation (see FIG. 3). The transmission shaft 31 has a square section 311 at one end fitted into a square slot 351 on the driving handle 35, and a screw rod 312 longitudinally extended from the square section 311 and screwed up with a nut 36. Therefore., the driving handle 35 is fixedly fastened to the transmission shaft 31 and retained between the nut 36 and the ratchet wheel housing 33.

The transmission cable 4 has one end coupled to the transmission shaft 31 in the middle thereof and an opposite end terminating into four equal branch cables 41 respectively wound around the link 17 and inserted through the through holes 181 on the steering rod 18 and then each respectively hooked on an ankle cradle 5 by a respective hook 411. The ankle cradles 5 each have a plurality of loops 51 for mounting the respective hook 411. Alternatively, the branch cables 41 may be directly fastened to the ankle cradles 5 without the use of the hooks 411. The ankle cradles 5 are respectively made of flexible material in the form of an elongated pad having fastening taps 52 and/or tie ropes 53 for fastening around the ankle of the leg.

Figure 4:
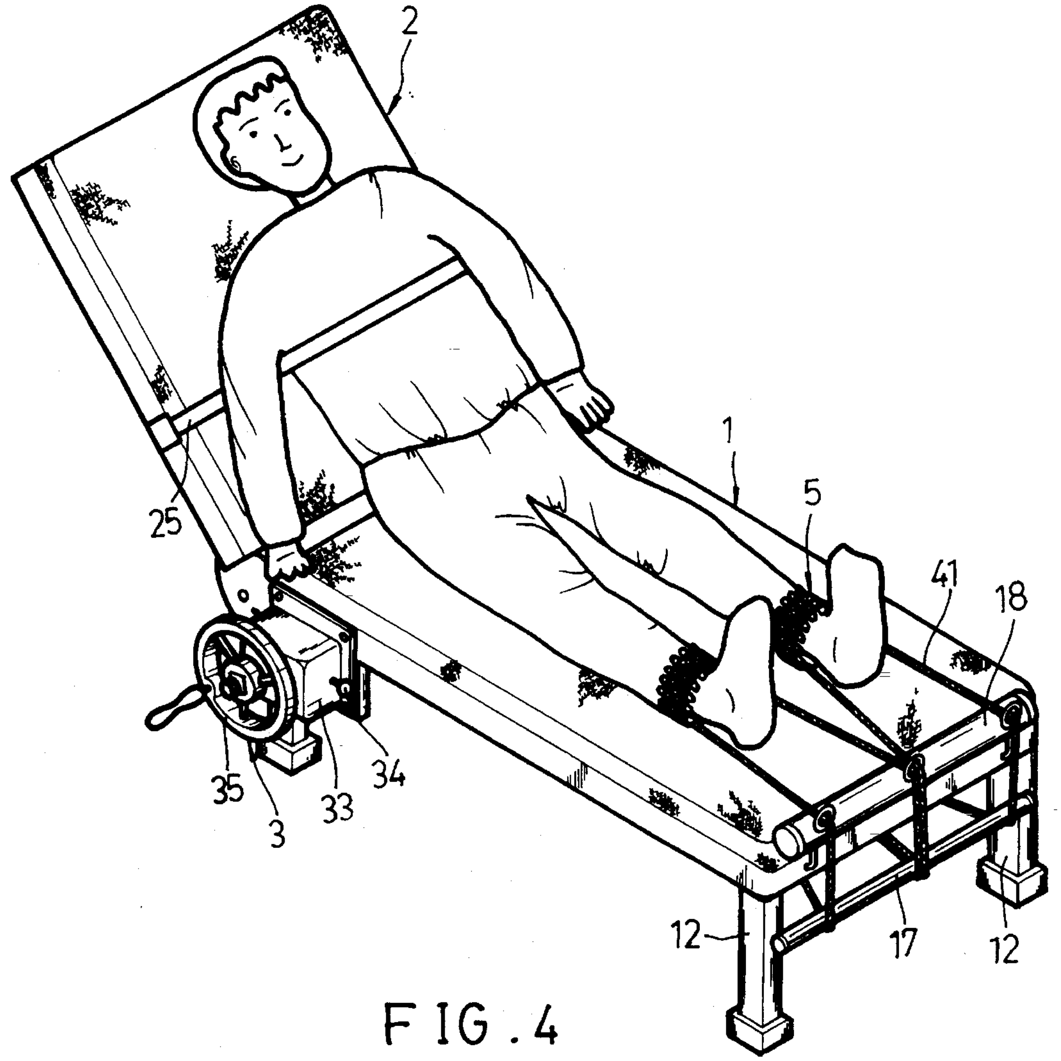
FIG. 4 is a perspective view of the present invention in use.

Referring to FIG. 4, when in use, the user is lying on the mattresses 11 and 21 and fastened in position by the strap 25. Then, the ankle cradles 5 are respectively fastened to the ankles of the user's legs. By adjusting the connection between the adjustment holes 141 and the bolt holes 231, the adjustable frame 2 is adjusted to the desired inclined position. When the driving handle 35 is turned, the ankle cradles 5 are pulled to drag the legs. After easy use, the pawl 34 can be released from the stub rod 15 permitting the ratchet wheel 32 to be turned in the reverse direction to release the tension of the transmission cable 4 for further application.

Figure 5:
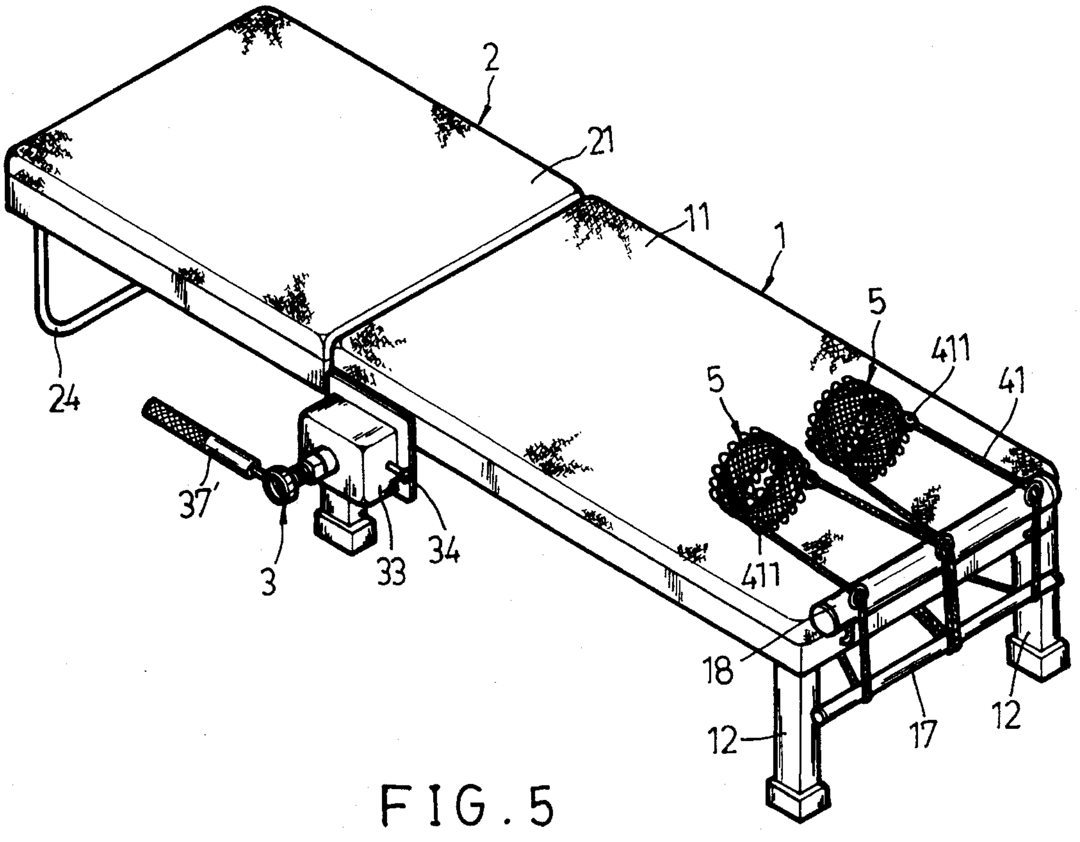
FIG. 5 shows an alternate form of the driving handle.

Referring to FIG. 5 and FIG. 4 again, the driving handle 35 can be a hand wheel 35 (as shown in FIG. 4) or a crank handle 37' (as shown in FIG. 5).

What is claimed is:

1. An apparatus for foot traction, comprising a folding bed, a transmission mechanism mounted on said folding bed at the bottom, and two ankle cradles driven by said transmission mechanism to pull the user's legs, wherein said transmission mechanism comprises a transmission shaft transversely mounted on said folding bed at the bottom, a transmission cable having one end fixedly fastened to said transmission shaft in the meddle and an opposite end terminating in symmetrical pairs of branch cables respectively fastened to said ankle cradles by hooks, a steering rod transversely disposed at one end of said folding bed for mounting the branch cables, said steering rod having a plurality of holes spaced along the length thereof through which the brand cables are inserted, a handle coupled to said transmission shaft at one end and driven to turn said transmission shaft in taking up said transmission cable, and means to stop said transmission cable from reverse rotation.

2. The apparatus of claim 1 wherein said stop means comprises a ratchet wheel fixedly mounted around said transmission shaft, and a pawl pivotally mounted on said folding bed and controlled to engage with the teeth of said ratchet wheel.

3. The apparatus of claim 1 wherein said handle is a hand wheel.

4. The apparatus of claim 1 wherein said handle is a crank handle.

* * * * *